(12) United States Patent
Rothermel et al.

(10) Patent No.: US 7,612,052 B2
(45) Date of Patent: Nov. 3, 2009

(54) COMBINATIONS COMPRISING EPOTHILONES AND PHARMACEUTICAL USES THEREOF

(75) Inventors: John David Rothermel, Sunset Beach, NC (US); Markus Wartmann, Riehen (CH); Jeanette Marjorie Wood, Biel-Benken (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/019,294

(22) Filed: Jan. 24, 2008

(65) Prior Publication Data
US 2008/0119529 A1 May 22, 2008

Related U.S. Application Data

(63) Continuation of application No. 10/484,482, filed as application No. PCT/EP02/08020 on Jul. 18, 2002, now abandoned.

(60) Provisional application No. 60/306,571, filed on Jul. 19, 2001, provisional application No. 60/306,559, filed on Jul. 19, 2001, provisional application No. 60/306,560, filed on Jul. 19, 2001.

(51) Int. Cl.
*A61K 31/66* (2006.01)
*A61K 31/425* (2006.01)
*A61K 31/28* (2006.01)

(52) U.S. Cl. ............... 514/102; 514/108; 514/365; 514/492

(58) Field of Classification Search ................ 514/102, 514/108, 365, 492
See application file for complete search history.

(56) References Cited

U.S. PATENT DOCUMENTS

| | | | |
|---|---|---|---|
| 2,409,754 A | 10/1946 | Henze | |
| 3,475,486 A | 10/1969 | Irani et al. | |
| 3,962,432 A | 6/1976 | Schmidt-Dunker | |
| 4,746,654 A | 5/1988 | Breliere et al. | |
| 4,814,326 A | 3/1989 | Rosini et al. | |
| 4,927,814 A | 5/1990 | Gall et al. | |
| 5,405,994 A | 4/1995 | Bonnery et al. | |
| 5,583,122 A | 12/1996 | Benedict et al. | |
| 5,849,726 A | 12/1998 | Brenner et al. | |
| 6,302,838 B1 | 10/2001 | O'Reilly et al. | |
| 2002/0061866 A1 | 5/2002 | Bataille et al. | |

FOREIGN PATENT DOCUMENTS

| FR | 2 775 187 A | 8/1999 |
|---|---|---|
| WO | WO 94 14455 | 7/1994 |
| WO | WO 98 35958 | 8/1998 |
| WO | WO 99 01124 A | 1/1999 |
| WO | WO 99 02514 A | 1/1999 |
| WO | WO 99 39694 A | 8/1999 |
| WO | WO 00 00485 A | 1/2000 |
| WO | WO 00 18439 A | 4/2000 |
| WO | WO 00 49019 A | 8/2000 |
| WO | WO 00 59485 A | 10/2000 |
| WO | WO 00 71104 A | 11/2000 |
| WO | WO 01 49295 A | 7/2001 |
| WO | WO 02 072085 | 9/2002 |

OTHER PUBLICATIONS

Stearns M. E. et al., "Effects of alendronate and taxol on PC-3 ML cell bone metastases in SCID mice," Invasion Metastasis, vol. 16(3), pp. 116-131 (1996).
Diel I. J. et al., "Reduction in new metastases in breast cancer with adjuvant clodronate treatment," New England Journal of Medicine, vol. 339(6), pp. 357-363 (1998).
Wood J. M. et al. "PTK787/ZK 222584, A novel and potent inhibitor of vascular endothelial growth factor receptor tyrosine kinases, impairs vascular endothelial growth factor-induced responses and tumor growth after oral administration," Cancer Research, vol. 60(8), pp. 2178-2189 (2000).
Schmidt P. et al., Tatsaechlicher Nutzen oder nur kein Schaden? Bisphosphonate in der Onkologie, Pharmacie in unserer Zeit, Nr. 6, pp. 519-527 (2001) (only available in German Language).
Yano et al., "Treatment for malignant pleural effusion of human lung adenocarcinoma by inhibition of vascular endothelial growth factor receptor tyrosine kinase phosphorylation," Clinical Cancer Research, vol. 6(3), pp. 957-965 (2000).

(Continued)

*Primary Examiner*—Raymond J Henley, III
(74) *Attorney, Agent, or Firm*—George R. Dohmann

(57) ABSTRACT

The invention relates to a combination which comprises (a) a bisphosphonate, a platinum compound or a vasculostatic compound and (b) an epothilone derivative of formula I (I)

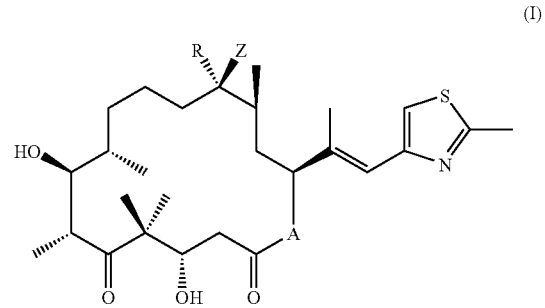

wherein A represents O or $NR_N$, wherein $R_N$ is hydrogen or lower alkyl, R is hydrogen or lower alkyl, and Z is O or a bond, in which the active ingredients (a) and (b) are present in each case in free form or in the form of a pharmaceutically acceptable salt and optionally at least one pharmaceutically acceptable carrier for simultaneous, separate or sequential use, in particular for the delay of progression or treatment of a proliferative disease, especially a solid tumor disease; a pharmaceutical composition, a commercial package or product comprising such a combination; the use of such a combination for the preparation of a medicament for the delay of progression or treatment of a proliferative disease and to a method of treatment of a warm-blooded animal.

9 Claims, No Drawings

OTHER PUBLICATIONS

Seiden M. V. et al., "Ovarian cancer," Oncologist, vol. 6(4), pp. 327-332 (2001).

Gillis R.A. et al., "Depression of cardiac synpathetic nerve activity by diphenylhydantoin," The Journal of Pharmacology and Experimental Therapeutics, vol. 179, pp. 599-610 (1971).

Quimby O. T. et al., "Tetrasodium carbonyldiphosphonate, synthesis, reactions, and spectral properties," J. Org. Chem., vol. 32, pp. 4111-4114 (1967).

Goodman & Gilman's, The Pharmacological Basis of Therapeutics, Ninth Edition, (1996), Calabresi, et al, Section X, Chemotherapy of Neoplastic Diseases, pp. 1225-1229.

COMBINATIONS COMPRISING EPOTHILONES AND PHARMACEUTICAL USES THEREOF

This is a continuation of application Ser. No. 10/484,482 filed on Jul. 9, 2004, which is a National Stage of International application No. PCT/EP2002/08020 filed on Jul. 18, 2002, which claims the benefit of U.S. Provisional Application No. 60/306,571 filed Jul. 19, 2001, U.S. Provisional Application No. 60/306,559 filed Jul. 19, 2001, and U.S. Provisional Application No. 60/306,560 filed Jul. 19, 2001, the entire disclosures of which are hereby incorporated by reference.

The invention relates to a combination which comprises (a) a bisphosphonate, a platinum compound or a vasculostatic compound and (b) an epothilone derivative of formula I and optionally at least one pharmaceutically acceptable carrier for simultaneous, separate or sequential use, in particular for the delay of progression or treatment of a proliferative disease, especially a solid tumor disease; a pharmaceutical composition comprising such a combination; the use of such a combination for the preparation of a medicament for the delay of progression or treatment of a proliferative disease; a commercial package or product comprising such a combination as a combined preparation for simultaneous, separate or sequential use; and to a method of treatment of a warm-blooded animal, especially a human.

Despite the widespread use of Taxol® and Taxotere® in the treatment of many different tumor types, the impact of taxanes on patient survival has been modest, and the overwhelming majority of metastatic tumors remain incurable. Taxane treatment is associated with a number of significant side-effects, such as peripheral neuropathy and stomatitis, and the effectiveness of taxanes can be severely limited by rapidly-developing drug resistance mechanisms, possibly involving tubulin mutations or overexpression of phosphoglycoproteins that function as drug efflux pumps. In view of these limitations as well as in view of the side-effects commonly observed with standard combination therapies, there is clearly a need for the identification of novel combinations that exhibit an improved overall profile including a broader spectrum of anti-tumor activity, efficacy against multi-drug resistant tumors and higher safety and tolerability.

The therapeutic efficacy of bisphosphonates has been demonstrated in the treatment of Paget's disease of bone, tumor-induced hypercalcaemia, bone metastasis and multiple myeloma (H. Fleisch in Bisphosphonates in Bone Disease. From the Laboratory to the Patient. Eds: The Parthenon Publishing Group, New York/London, 1997, p. 68 to 163).

Direct evidence of the role of the "Vascular Endothelial Growth Factor" (VEGF) as a tumour angiogenesis factor in vivo has been obtained from studies in which VEGF expression or VEGF activity was inhibited. This was achieved with antibodies which inhibit VEGF activity, with dominant-negative VEGFR-2 mutants which inhibited signal transduction, or with the use of antisense-VEGF RNA techniques. Small molecules inhibiting the VEGF tyrosine kinase are disclosed, e.g., in WO98/35958. One of these molecules is known as PTK787.

The microtubule-stabilizing effect of epothilones was first described by Bollag et al., Cancer Research 55, 1995, 2325-33. A suitable treatment schedule of different types of tumors, especially tumors which are refractory to the treatment by other chemotherapeutics, in particular TAXOL™, is described in WO 99/43320.

The present invention pertains to a combination, such as a combined preparation or a pharmaceutical composition, which comprises (a) a bisphosphonate, a platinum compound or a vasculostatic compound and (b) an epothilone derivative of formula I

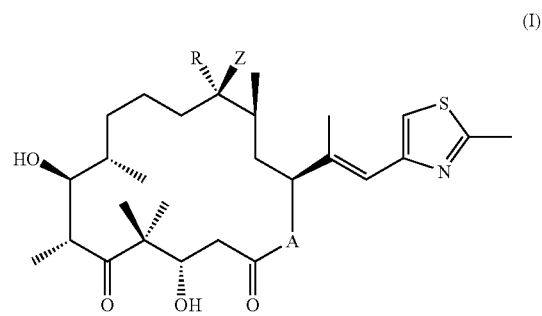

wherein A represents O or $NR_N$, wherein $R_N$ is hydrogen or lower alkyl, R is hydrogen or lower alkyl, and Z is O or a bond, in which the active ingredients (a) and (b) are present in each case in free form or in the form of a pharmaceutically acceptable salt and optionally at least one pharmaceutically acceptable carrier; for simultaneous, separate or sequential use.

Unless stated otherwise, in the present disclosure organic radicals and compounds designated "lower" contain not more than 7, preferably not more than 4, carbon atoms.

A compound of formula I wherein A represents O, R is hydrogen and Z is O is known as epothilone A; a compound of formula I wherein A represents O, R is methyl and Z is O is known as epothilone B; a compound of formula I wherein A represents O, R is hydrogen and Z is a bond is known as epothilone C; a compound of formula I wherein A represents O, R is methyl and Z is a bond is known as epothilone D.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutical effect in a non-effective dosage of one or both of the combination partners (a) and (b), and very preferably a strong synergism of the combination partners (a) and (b).

The term "solid tumor disease" especially means breast cancer, ovarian cancer, cancer of the colon and generally the GI tract including gastric cancer, cervix cancer, lung cancer, e.g. small-cell lung cancer and non-small-cell lung cancer, pancreas cancer, renal cancer, glioma, melanoma, head and neck cancer, bladder cancer, hepatocellular cancer, prostate cancer and Kaposi's sarcoma. Preferably, the proliferative disease to be treated with a combination comprising a platinum compound is ovarian cancer, lung cancer, head or neck cancer, cervix cancer, prostate cancer, colon cancer, breast cancer, renal cancer, carcinoid tumors, gastric cancer or hepatocellular cancer. Preferably, the proliferative disease to be treated with a combination comprising a bisphosphonate is breast cancer, ovarian cancer or lung cancer. In another preferred embodiment of the invention, the proliferative disease to be treated with a COMBINATION OF THE INVENTION comprising a vasculostatic compound, in particular PTK787, is ovarian cancer, breast cancer, lung cancer, head or neck cancer, cervix cancer, prostate cancer or colon cancer.

The term "proliferative disease" as used herein comprises the solid tumor diseases as listed above and furthermore Paget's disease of bone, tumor-induced hypercalcaemia, bone metastasis and multiple myeloma.

The term "a disease associated with deregulated angiogenesis" relates especially to diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), neurodegenerative disorders, and especially proliferative diseases, especially those proliferative diseases comprising tumours expressing c-kit, KDR or flt-1.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "platinum compound" as used herein means carboplatin, cisplatin or oxaliplatin.

The term "carboplatin" as used herein relates to the antineoplastic agent cis-diamine (1,1-cyclobutane dicarboxylato) platinum(II), which is disclosed, e.g., in U.S. Pat. No. 4,140,707 or by R. C. Harrison et al. in Inorg. Chim. Acta 46, L15 (1980). This drug can be administered e.g., in the form as it is marketed, e.g. under the trademark CARBOPLAT™ or PARAPLATIN™.

The term "oxaliplatin" as used herein relates to the antineoplastic agent also known as oxalatoplatinum, which is disclosed, e.g., in U.S. Pat. No. 5,716,988. This drug can be administered e.g., in the form as described in the cited US patent or in the form it is marketed, e.g. under the trademark ELOXANTINE™ or 1-OHP™.

The term "cisplatin" as used herein relates to the antineoplastic agent also known as cis-diaminedichloroplatinum, which compound and its use as antineoplastic agent is disclosed, e.g., in DE 2,318,020.

The term "vasculostatic compounds" as used herein comprises, but is not restricted to, active ingredients which decrease the activity of the VEGF, metalloproteinase inhibitors and other compounds having a vasculostatic effect.

The active ingredient, which decreases the activity of the VEGF, is especially selected from the group consisting of compounds which inhibit the VEGF receptor tyrosine kinase, compounds which inhibit a VEGF receptor and compounds binding to VEGF. The active ingredient, which decreases the activity of the VEGF, is in particular one of those compounds, proteins and monoclonal antibodies, which are generically and specifically disclosed in WO 98/35958 (describing compounds of formula II), WO 00/09495, WO 00/27820, WO 00/59509, WO 98/11223, WO 00/27819, WO 01/55114, WO 01/58899 and EP 0 769 947, which are described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999, those which are generically and specifically disclosed in WO 00/37502 and WO 94/10202; and those which are described by M. S. O'Reilly et al, Cell 79, 1994, 315-328 (Angiostatin™) and by M. S. O'Reilly et al, Cell 88, 1997, 277-285 (Endostatin™), in each case in particular in the compound claims, the pharmaceutical preparations and the final products of the working examples, the subject-matter of which is hereby incorporated into the present application by reference to this publications. Comprised are likewise the corresponding stereoisomers as well as the corresponding crystal modifications, e.g. solvates and polymorphs, which are disclosed therein. The compounds used as active ingredients in the combinations disclosed herein can be prepared and administered as described in the cited documents, respectively.

The term "PTK787" as used herein means a compound of formula II

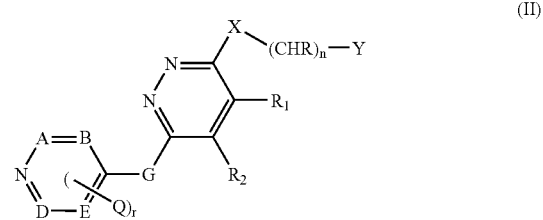

(II)

wherein r, n and m are each O, $R_1$ and $R_2$ together form a bridge of subformula II*,

(II*)

A, B, D and E are each CH, G is methylene, X is imino, Y is 4-chlorophenyl, and the bonds characterized by a wavy line are double bonds, disclosed, e.g., in Example 38 of WO98/

35958. Preferably, such compound is employed in the form of its succinate salt. This drug or its salt can be administered, e.g., in the form as disclosed in the cited PCT patent application.

"Metalloproteinase inhibitors" as defined herein are, e.g., Marimastat (BB-2516), Prinomastat (AG3340), Bay 12-9566, BMS-275291, MMI270B and Metastat (NSC 683551).

The term "other compounds having a vasculostatic effect" as defined herein relates in particular to the compounds EMD-121974, doxorubicin, paclitaxel, IM-862, Thalidomide®, Linomide®, PKC412, AGM-1470, Suramin and Pentosan polysulfate.

Epothilone derivatives of formula I wherein A represents O or $NR_N$, wherein $R_N$ is hydrogen or lower alkyl, R is hydrogen or lower alkyl and Z is O or a bond, and methods for the preparation of such epothilone derivatives are in particular generically and specifically disclosed in the patents and patent applications WO 93/10121, U.S. Pat. No. 6,194,181, WO 98/25929, WO 98/08849, WO 99/43653, WO 98/22461 and WO 00/31247 in each case in particular in the compound claims and the final products of the working examples, the subject-matter of the final products, the pharmaceutical preparations and the claims is hereby incorporated into the present application by reference to this publications. Comprised are likewise the corresponding stereoisomers as well as the corresponding crystal modifications, e.g. solvates and polymorphs, which are disclosed therein. Epothilone derivatives of formula I, especially epothilone B, can be administered as part of pharmaceutical compositions which are disclosed in WO 99/39694.

The transformation of epothilone B to the corresponding lactam is disclosed in Scheme 21 (page 31, 32) and Example 3 of WO 99/02514 (pages 48-50). The transformation of a compound of formula I which is different from epothilone B into the corresponding lactam can be accomplished analogously. Corresponding epothilone derivatives of formula I wherein $R_N$ is lower alkyl can be prepared by methods known in the art such as a reductive alkylation reaction starting from the epothilone derivative wherein $R_N$ is hydrogen.

Furthermore, the structure of the active agents mentioned herein by name may be taken from the actual edition of the standard compendium "The Merck Index" or from databases, e.g. Patents International (e.g. IMS World Publications). The corresponding content thereof is hereby incorporated by reference. Any person skilled in the art is fully enabled, based on these references, to manufacture and test the pharmaceutical indications and properties in standard test models, both in vitro and in vivo.

The compounds used as combination partners (a) and (b) disclosed herein can be prepared and administered as described in the cited documents, respectively.

It will be understood that references to the combination partners (a) and (b) are meant to also include the pharmaceutically acceptable salts. If these combination partners (a) and (b) have, for example, at least one basic center, they can form acid addition salts. Corresponding acid addition salts can also be formed having, if desired, an additionally present basic center. The combination partners (a) and (b) having an acid group (for example COOH) can also form salts with bases. The combination partner (a) or (b) or a pharmaceutically acceptable salt thereof may also be used in form of a hydrate or include other solvents used for crystallization.

A combination which comprises (a) a bisphosphonate, a platinum compound or a vasculostatic compound and (b) an epothilone derivative of formula I in which compound A represents O or $NR_N$, wherein $R_N$ is hydrogen or lower alkyl, R is hydrogen or lower alkyl, and Z is O or a bond, in which the active ingredients are present in each case in free form or in the form of a pharmaceutically acceptable salt and optionally at least one pharmaceutically acceptable carrier, will be referred to hereinafter as a COMBINATION OF THE INVENTION.

The COMBINATIONS OF THE INVENTION inhibits the growth of solid tumors, but also liquid tumors. In one preferred embodiment of the invention, the disease to be treated is prostate cancer, in particular hormone refractory prostate cancer with bone metastasis. Furthermore, a COMBINATIONS OF THE INVENTION comprising a vasculostatic compound, in particular PTK787, exhibit beneficial effects in the treatment of diseases associated with deregulated angiogenesis.

The nature of proliferative diseases like solid tumor diseases is multifactorial. Under certain circumstances, drugs with different mechanisms of action may be combined. However, just considering any combination of drugs having different mode of action does not necessarily lead to combinations with advantageous effects.

All the more surprising is the experimental finding that in vivo the administration of a COMBINATION OF THE INVENTION compared to a monotherapy applying only one of the pharmaceutically active ingredients used in the COMBINATION OF THE INVENTION results not only in a more beneficial, especially synergistic, anti-proliferative effect, e.g. with regard to the delay of progression of a proliferative disease or with regard to a change in tumor volume, and/or more beneficial, especially synergistic, effect of preventing skeletal-related events (SREs), but also in further surprising beneficial effects, e.g. less side-effects and a decreased mortality and morbidity. Furthermore, depending on the tumor type and the particular combination used a decrease of the tumor volume can be obtained when using a COMBINATION OF THE INVENTION in cases in which by monotherapy no decrease of the tumor volume can be achieved. The COMBINATIONS OF THE INVENTION are also suitable to prevent the metastatic spread of tumors and the growth or development of micrometastases. The COMBINATION OF THE INVENTION are in particular suitable for the treatment of poor prognosis patients, i.e. in particular such patients that did not respond to or relapse after an earlier treatment with a single drug or a combination different to a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side-effects. This is in accordance with the desires and requirements of the patients to be treated.

It can be shown by established test models and in particular those test models disclosed herein that a COMBINATION OF THE INVENTION results in the beneficial effects described herein-before. The person skilled in the pertinent art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are in particular randomized, double-blind, placebo-controlled, parallel studies. Such studies are, in particular, suitable to compare the effects of a monotherapy using the active ingredients and a therapy using a COMBINATION OF THE INVENTION, and to prove in particular the synergism of the active ingredients of the COMBINATIONS OF THE INVENTION. The beneficial effects on proliferative diseases, e.g. to prevent skeletal-related events (SREs) in prostate cancer patients with a history of metastatic bone disease, can be determined directly through the results of these studies or by changes in the study design which are known as such to a person skilled in the art. SREs are defined as pathologic bone fracture events, spinal cord compression events, surgery to bone, radiation therapy to bone and a change of antineoplastic therapy to treat bone pain. Preferably, SREs are the primary endpoints in such studies. Furthermore, in such studies the effect on pain scores, analgesic use, performance status, Quality of Life scores, bone mineral density, time to progression in bone and overall progression can be evaluated.

In a suitable study design, patients are randomized in a double-blind fashion to receive every three weeks either 2 mg zoledronate intravenously as a 5-minute infusion or 15-minute infusion, 4 mg zoledronate intravenously as a 5-minute infusion or 15-minute infusion, or a placebo intravenously as a 5-minute infusion or 15-minute infusion, in addition to a compound of formula I, e.g. 6 cycles of epothilone B wherein each cycle consists of between 2.5 mg/m$^2$ and 6 mg/m$^2$ epothilone B administered as a 5 minute bolus once a week for three weeks followed by 14 days of rest.

In another suitable study design, patients are randomized in a double-blind fashion to receive every two weeks 45 mg oxaliplatin/m$^2$ body surface intravenously as a 2 to 6 hour infusion or a corresponding placebo in addition to a compound of formula I, e.g. 6 cycles of epothilone B wherein each cycle consists of 2.5 mg/m$^2$ epothilone B administered as a 5 minute bolus once a week for three weeks followed by 14 days of rest.

In a further suitable study design, patients are randomized in a double-blind fashion to receive daily, e.g., 250 or 500 mg PTK787 or a corresponding placebo in addition to a compound of formula I, e.g. 6 cycles of epothilone B wherein each cycle consists of 2.5 mg/m$^2$ epothilone B administered as a 5 minute bolus once a week for three weeks followed by 14 days of rest.

In another study design, weekly doses of 0.5 mg/m$^2$, 1.0 mg/m$^2$, 1.5 mg/m$^2$, 2.0 mg/m$^2$ or 2.5 mg/m$^2$ of epothilone B are applied as intravenous infusion over 5 minutes and cisplatin is dosed per standard guidelines, i.e. in a weekly dose of 20-100 mg/m$^2$ of body surface area, e.g. 30 mg/m$^2$ weekly. The cisplatin injection is diluted prior to administration and administered immediately after epothilone B as a one-hour intravenous infusion. One cycle of treatment consists of the administration of both drugs for three weeks followed by one week of rest.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils, alcohols, flavoring agents, preservatives, coloring agents; or carriers such as starches, sugars, microcristalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

In particular, a therapeutically effective amount of each of the combination partners of the COMBINATION OF THE INVENTION may be administered simultaneously or sequentially and in any order, and the components may be administered separately or as a fixed combination. For example, the method of delay of progression or treatment of a proliferative disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

If the warm-blooded animal is a human, the dosage of a compound of formula I is preferably in the range of about 0.25 to 75, preferably 0.5 to 50, e.g. 2.5, mg/m² once weekly for two to four, e.g. three, weeks, followed by 6 to 8 days off in the case of an adult patient.

Epothilone B is preferably administered in a dose which is calculated according to the formula (III)

$$\text{single dose (mg/m2)}=(0.1 \text{ to } y)\times N \quad (III)$$

wherein N is the number of weeks between treatments and y is 6, wherein epothilone B is administered in more than one treatment cycle after an interval of one week to six weeks after the preceding treatment.

In one preferred embodiment of the invention, epothilone B is administered weekly in a dose that is between about 0.1 to 6 mg/m², preferably between 0.1 and 3 mg/m², e.g. 2.5 or 3.0 mg/m², for three weeks after an interval of one to six weeks, especially an interval of one week, after the preceding treatment. In another embodiment of the invention said epothilone B is preferably administered to a human every 18 to 24 days in a dose that is between about 0.3 and 12 mg/m².

Unless stated otherwise herein, the bisphosphonates described herein can be administered in the following dosages:

Alendronic acid may be administered to a human in a dosage range varying from about 5 to 10 mg/day.

Clodronic acid may be administered to a human e.g. in a dosage range varying from about 750 to 1500 mg/day.

Etridonic acid may be administered to a human in a dosage range varying from about 200 to 400 mg/day.

Ibandronic acid may be administered to a human in a dosage range varying from about 1 to 4 mg every three to four weeks.

Risedronic acid may be administered to a human in a dosage range varying from about 20 to 30 mg/day.

Pamidronic acid may be administered to a human in a dosage range varying from about 15 to 90 mg every three to four weeks.

Tiludronic acid may be administered to a human in a dosage range varying from about 200 to 400 mg/day.

Zoledronic acid may be administered to a human in a dosage range varying from about 2 to 10 mg, especially 4 or 8 mg, as an intravenous infusion every 3 weeks.

Carboplatin may be administered intravenously to a human in a dosage range varying from about 100 to 400, e.g. 200, mg/m² body surface about every four to six weeks.

Oxaliplatin may be administered intravenously to a human in a dosage range varying from about 25 to 135, e.g. 45 or 85, mg/m² body surface about every two to three weeks.

Cisplatin may be administered to a human in a dosage range varying from about 25 to 100 mg/m² about every three weeks.

If the warm-blooded animal is a human, the dosage of PTK787 is preferably in the range of about 50 to 1500, more preferably about 100 to 750, and most preferably 250 to 500, mg/day.

In a preferred embodiment of the invention, the COMBINATION OF THE INVENTION comprises a bisphosphonate selected from etridonic acid, clodronic acid, tiludronic acid, pamidronic acid, alendronic acid, ibandronic acid, risedronic acid and, most preferably, zoledronic acid.

In another embodiment of the invention, the COMBINATION OF THE INVENTION comprises cisplatin, oxaliplatin or carboplatin.

In another embodiment of the invention, the COMBINATION OF THE INVENTION comprises a vasculostatic of formula II
wherein r is 0 to 2, n is 0 to 2, m is 0 to 4,
$R_1$ and $R_2$ (i) are lower alkyl or
(ii) together form a bridge in subformula II* the binding being achieved via the two terminal carbon atoms, or
(iii) together form a bridge in subformula II*

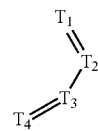

(II**)

wherein one or two of the ring members $T_1$, $T_2$, $T_3$ and $T_4$ are nitrogen, and the others are in each case CH, and the binding is achieved via $T_1$ and $T_4$;

A, B, D, and E are, independently of one another, N or CH, with the stipulation that not more than 2 of these radicals are N;

G is lower alkylene, lower alkylene substituted by acyloxy or hydroxy, —CH$_2$—O—, —CH$_2$—S—, —CH$_2$—NH—, oxa (—O—), thia (—S—), or imino (—NH—);

Q is lower alkyl;

R is H or lower alkyl;

X is imino, oxa, or thia;

Y is unsubstituted or substituted aryl, pyridyl, or unsubstituted or substituted cycloalkyl; and Z is amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfonyl, phenyl-lower alkylsulfinyl or alkylphenylsulfinyl, substituents Z being the same or different from one another if more than 1 radical Z is present;

and wherein the bonds characterized, if present, by a wavy line are either single or double bonds;

or an N-oxide of the defined compound, wherein 1 or more N atoms carry an oxygen atom, or the salt of such compound having at least one salt-forming group. Preferably, the compound of formula II to be employed is PTK787.

The terms used for the definition of the compound of formula II have the meanings as defined in WO98/35958, which definitions are herein included by reference.

In the compound of formula I preferably A represents O. R is lower alkyl, e.g. ethyl or, most preferably, methyl. Z is preferably O.

The COMBINATION OF THE INVENTION can be a combined preparation or a pharmaceutical composition.

Moreover, the present invention relates to a method of treating a warm-blooded animal having a proliferative disease, in particular prostate cancer, especially hormone refractory prostate cancer with bone metastasis, comprising administering to the animal a COMBINATION OF THE INVENTION in a quantity which is jointly therapeutically effective against a proliferative disease and in which the combination partners can also be present in the form of their pharmaceutically acceptable salts.

Furthermore, the present invention pertains to the use of a COMBINATION OF THE INVENTION for the delay of progression or treatment of a proliferative disease and for the preparation of a medicament for the delay of progression or treatment of a proliferative disease.

Additionally, the present invention pertains to the use of a bisphosphonate, a platinum compound or a vasculostatic compound in combination with an epothilone derivative of formula I in which compound A represents O or $NR_N$, wherein $R_N$ is hydrogen or lower alkyl, R is hydrogen or lower alkyl, and Z is O or a bond, for the preparation of a medicament for the delay of progression or treatment of a proliferative disease.

Moreover, the present invention provides a commercial package comprising as active ingredients COMBINATION OF THE INVENTION, together with instructions for simultaneous, separate or sequential use thereof in the delay of progression or treatment of a proliferative disease.

The following Examples illustrate the invention described above; they are not, however, intended to limit the scope of the invention in any way. The beneficial effects of the COMBINATION OF THE INVENTION can also be determined by other test models known as such to the person skilled in the pertinent art.

EXAMPLE 1

PC-3MM2 Human Prostate Carcinoma Cells Grown Intratibia in Nude Mice

A cell suspension ($2\times10^5$ cells) of the human prostate carcinoma line PC-3MM2 is injected into the tibia of nude mice. The growth of the tumor in this model leads to bone destruction that is clearly visible after 4 weeks. Treatment with the compounds is started 7 days after injection of the tumor cells. At this time animals are sorted into groups with equivalent mean and range of tumor sizes. Treatment is then randomized to the different groups and treated with vehicles only; with (a) a bisphosphonate, e.g. zoledronic acid; a combination partner (b), e.g. epothilone B; or the combined partners (a) and (b), e.g. zoledronic acid and epothilone B. Analysis after 3-4 weeks of treatment includes estimation of bone destruction and tumor load.

EXAMPLE 2

Bisphosphonate and an Epothilone in DU145 Human Prostate Carcinoma Tumor fragments Grown S.C. in Nude Mice DU145 human prostate carcinoma tumors are grown s.c. in nude mice. Tumor fragments (approximately 25 mg each) are implanted subcutaneously (s.c.) into the left flank of nude mice. Treatment with the compounds is started when tumors reach a size of 80-100 mm$^2$ (usually after 10-15 days). At this time animals are sorted into groups with equivalent mean and range of tumor sizes. Treatment is then randomized to the different groups and treated with vehicles only; with (a) a bisphosphonate e.g. zoledronic acid; a combination partner (b), e.g. epothilone B; or the combined partners (a) and (b), e.g. zoledronic acid and epothilone B. Tumor size (measured with calipers) and body weight are assessed every 3-5 days.

EXAMPLE 3

Oxaliplatin and Epothilone B in DU145 Human Prostate Carcinoma Tumor Fragments Grown s.c. in Nude Mice DU145 human prostate carcinoma tumors are grown s.c. in nude mice. Tumor fragments (approximately 25 mg each) are implanted subcutaneously (s.c.) into the left flank of nude mice. Treatment with the compounds is started when tumors reach a size of 80-100 mm$^2$ (usually after 10-15 days). At this time animals are sorted into groups with equivalent mean and range of tumor sizes. Treatment is then randomized to the different groups and treated with vehicles only; with (a) oxaliplatin; (b) epothilone B; or the combined partners (a) and (b), administered either simultaneously or sequentially in any order. Tumor size (measured with calipers) and body weight are assessed every 3-5 days.

EXAMPLE 4

Carboplatin and Epothilone B in NCI-H596 Human Lung Cancer Tumor Fragments Grown S.C. in Nude Mice In the same model as used in Example 3, but employing the lung tumor cell line NCI-H596, the superior efficacy of the combination consisting of carboplatin and epothilone B compared to the single drugs can be demonstrated.

EXAMPLE 5

PTK787 and Epothilone B in DU145 Human Prostate Carcinoma Subcutaneous Xenografts in Nude Mice DU145 human prostate carcinoma cells are grown s.c. in nude mice. Tumor cell ($10^6$) are injected subcutaneously (s.c.) into the left and right flanks of nude mice. Treatment with the compounds is started after 25-32 days when tumors reach a size of 80-100 mm$^2$. At this time animals are sorted into groups with equivalent mean and range of tumor sizes. Treatment is then randomized to the different groups and treated with vehicles only; with 2 mg/kg epothilone B given once a week intravenously; 50 mg/kg PTK787 administered once a day p.o.; or the combined partners epothilone B and PTK787. Tumor size and body weight changes are measured with calipers on a weekly basis. The results show additive tumor growth inhibition without concomitant increased body weight loss.

EXAMPLE 6

Epothilone B and PTK787 in B16 Syngeneic Mouse Melanoma Subcutaneous Xenografts in Black Mice B16 mouse melanoma cells ($5\times10^4$) are injected subcutaneously (s.c.) into the ears of black mice. Treatment with the compounds is started after 7 days. At this time animals are sorted into groups with equivalent mean and range of tumor sizes. Treatment is then randomized to the different groups and treated with vehicles only; with epothilone B given once a week intravenously; with PTK787 administered once a day p.o.; or the combined partners epothilone B and PTK787. Primary tumor growth is monitored on a weekly basis by computer-assisted analysis of photographic images of melanomas. Animals are necropsized 3 weeks after treatment initiation. Metastatic spread is assessed by weighing of cervical lymph nodes.

What is claimed is:

1. A combination which comprises (a) a vasculostatic compound which is a VEGFR inhibitor and (b) an epothilone derivative of formula I

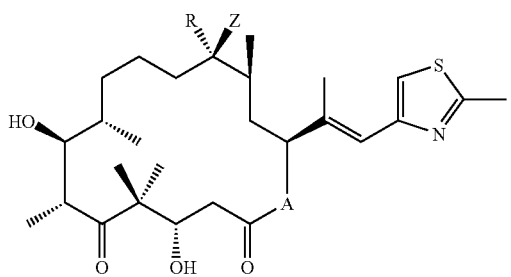

(I)

wherein A represents O or $NR_N$, wherein $R_N$ is hydrogen or lower alkyl, R is hydrogen or lower alkyl, and Z is O or a bond,
  in which the active ingredients (a) and (b) are present in each case in free form or in the form of a pharmaceutically acceptable salt and optionally at least one pharmaceutically acceptable carrier; for simultaneous, separate or sequential use.

2. Combination according to claim 1 wherein the vasculostatic compound is PTK787.

3. Combination according to claim 1 comprising an epothilone derivative of formula I wherein A represents O, R is lower alkyl or hydrogen and Z is O or a bond.

4. Combination according to claim 1, which is a combined preparation or a pharmaceutical composition.

5. Method of treating a warm-blooded animal having a solid tumor disease comprising administering to the animal a combination according to claim 1 in a quantity which is jointly therapeutically effective against a proliferative disease and in which the compounds can also be present in the form of their pharmaceutically acceptable salts.

6. Method of treating according to claim 5 wherein PTK787 is employed and the solid tumor disease is ovarian cancer, lung cancer, head or neck cancer, cervix cancer, prostate cancer or colon cancer.

7. A pharmaceutical composition comprising a quantity which is jointly therapeutically effective against a solid tumor disease of a pharmaceutical combination according to claim 1 and at least one pharmaceutically acceptable carrier.

8. A commercial package comprising (a) a vasculostatic compound which is a VEGFR inhibitor and (b) an epothilone derivative of formula I

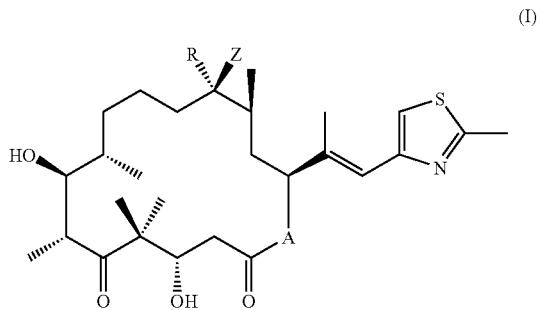

(I)

wherein A represents O or $NR_N$, wherein $R_N$ is hydrogen or lower alkyl, R is hydrogen or lower alkyl, and Z is O or a bond,
  together with instructions for simultaneous, separate or sequential use thereof in the delay of progression or treatment of a solid tumor disease.

9. A combination of claim 2 wherein the epothilone derivative is epothilone B.

* * * * *